(12) United States Patent
Zhang et al.

(10) Patent No.: US 11,141,454 B2
(45) Date of Patent: Oct. 12, 2021

(54) APPLICATION OF EARTHWORM PROTEIN PEPTIDE IN PREPARATION OF MEDICINE FOR PREVENTING AND/OR TREATING THROMBOTIC DISEASE

(71) Applicant: Zhongshiduqing (Shandong) Biotech Co., Ltd., Shandong (CN)

(72) Inventors: Jiuxun Zhang, Shandong (CN); Xuejun Zhang, Shandong (CN); Mingzhan Tian, Shandong (CN); Xiping Zhang, Shandong (CN); Wei Wei, Shandong (CN)

(73) Assignee: ZHONGSHIDUQING (SHANDONG) BIOTECH CO., LTD., Shandong (CN)

( * ) Notice: Subject to any disclaimer, the term of this patent is extended or adjusted under 35 U.S.C. 154(b) by 0 days.

(21) Appl. No.: 16/839,425

(22) Filed: Apr. 3, 2020

(65) Prior Publication Data

US 2021/0138022 A1    May 13, 2021

(30) Foreign Application Priority Data

Nov. 12, 2019  (CN) .......................... 201911098946.5

(51) Int. Cl.
| | |
|---|---|
| *A61K 38/07* | (2006.01) |
| *A61K 38/08* | (2019.01) |
| *A61K 38/10* | (2006.01) |
| *A61P 7/02* | (2006.01) |
| *C07K 7/06* | (2006.01) |
| *C07K 7/08* | (2006.01) |
| *C07K 14/00* | (2006.01) |

(52) U.S. Cl.
CPC .............. *A61K 38/07* (2013.01); *A61P 7/02* (2018.01)

(58) Field of Classification Search
CPC ........ A61K 38/07; A61K 38/08; A61K 38/10; A61P 7/02; C07K 7/06; C07K 7/08; C07K 14/00

USPC ....... 530/300, 324, 325, 326, 327, 328, 329, 530/330; 514/1.1, 13.6, 13.7, 21.8, 21.7, 514/21.6, 21.5, 21.4, 21.3

See application file for complete search history.

(56) References Cited

U.S. PATENT DOCUMENTS

| | | | |
|---|---|---|---|
| 6,703,491 B1 * | 3/2004 | Homburger ........ | A01K 67/0333 435/252.3 |
| 7,049,485 B2 * | 5/2006 | Sticklen ......... | C12Y 302/01004 800/288 |
| 9,075,059 B2 * | 7/2015 | Kelly ....................... | A61P 35/04 |
| 9,422,335 B2 * | 8/2016 | Long ..................... | A61K 38/10 |

OTHER PUBLICATIONS

Overview of Thrombotic Disorders from Merck Manual, pp. 1-4. Accessed Jan. 6, 2021. (Year: 2021).*

* cited by examiner

*Primary Examiner* — Julie Ha

(74) *Attorney, Agent, or Firm* — Onello & Mello, LLP

(57) ABSTRACT

Provided is an earthworm protein peptide for preparing a medicine for treating a thrombotic disease. The earthworm protein peptide is any one selected from a group consisting of Leu-Val-Thr-Leu-Gly-Asn-Glu (SEQ ID NO.: 1), Leu-Leu-Ala-Pro-Pro (SEQ ID NO: 2), Leu-Leu-Pro-Ala-Pro (SEQ ID NO: 3) and Thr-Val-Ala-Pro-Phe (SEQ ID NO: 4). The earthworm protein peptide can significantly inhibit the thrombin activity, thus achieving the anticoagulant effect. In vivo, the earthworm protein peptide has a significant inhibitory effect on carrageenan-induced rat tail thrombosis; and in vitro and in vivo studies of rats with thrombus, the earthworm protein peptide provided by the present invention shows good anticoagulant effects. The earthworm protein peptide has effects of thrombosis inhibition, thrombolysis, anticoagulation and fibrinolysis promotion, and can effectively prevent and treat thrombotic disease.

9 Claims, 17 Drawing Sheets

Specification includes a Sequence Listing.

Earthworm protein peptide low-dose group

Earthworm protein peptide prevention group

Earthworm protein peptide high-dose group

Earthworm protein peptide medium-dose group

SEQUENCE LISTING

```
<160> NUMBER OF SEQ ID NOS: 4

<210> SEQ ID NO 1
<211> LENGTH: 7
<212> TYPE: PRT
<213> ORGANISM: artificial sequence
<220> FEATURE:
<223> OTHER INFORMATION: an amino acid sequence of the first earthworm
``` protein peptide

<400> SEQUENCE: 1

Leu Val Thr Leu Gly Asn Glu
1               5

<210> SEQ ID NO 2
<211> LENGTH: 5
<212> TYPE: PRT
<213> ORGANISM: artificial sequence
<220> FEATURE:
<223> OTHER INFORMATION: an amino acid sequence of the second earthworm
      protein peptide

<400> SEQUENCE: 2

Leu Leu Ala Pro Pro
1               5

<210> SEQ ID NO 3
<211> LENGTH: 5
<212> TYPE: PRT
<213> ORGANISM: artificial sequence
<220> FEATURE:
<223> OTHER INFORMATION: an amino acid sequence of the third earthworm
      protein peptide

<400> SEQUENCE: 3

Leu Leu Pro Ala Pro
1               5

<210> SEQ ID NO 4
<211> LENGTH: 5
<212> TYPE: PRT
<213> ORGANISM: artificial sequence
<220> FEATURE:
<223> OTHER INFORMATION: an amino acid sequence of the fourth earthworm
      protein peptide

<400> SEQUENCE: 4

Thr Val Ala Pro Phe
1               5

APPLICATION OF EARTHWORM PROTEIN PEPTIDE IN PREPARATION OF MEDICINE FOR PREVENTING AND/OR TREATING THROMBOTIC DISEASE

SEQUENCE LISTING

A sequence listing file named SeqListing_ST25.txt is filed herewith forms part of this application and is incorporated herein by reference. The sequence listing file SeqListing_ST25.txt was created on Nov. 12, 2019 and has a size of 1.15 KB.

CROSS REFERENCE TO RELATED APPLICATIONS

The present application claims the benefit of priority under 35 USC 119 to Chinese patent application 201911098946.5, filed Nov. 12, 2019, the contents of which are incorporated herein by reference.

TECHNICAL FIELD

The present invention relates to the technical field of prevention and treatment of cardiovascular and cerebrovascular diseases, and in particular to application of an earthworm protein peptide in the preparation of a medicine for preventing and/or treating a thrombotic disease.

BACKGROUND

Diseases caused by two pathological processes of thrombosis and thromboembolism are clinically called thrombotic diseases. The thrombotic diseases are a serious threat to human life and health, and the incidence rate thereof is the highest among various diseases. In recent years, there has been increasing interest in preventing and treating thrombotic diseases, and this field has become one of the principal focuses and hotspots of contemporary medical research.

Conventional antithrombotic medicines mainly include anticoagulant medicines, antiplatelet medicines and thrombolytic medicines. Although these medicines have varying degrees of effectiveness, existing treatments are not ideal.

SUMMARY

An objective of the present invention is to provide application of an earthworm protein peptide in the preparation of a medicine for preventing and/or treating a thrombotic disease. The earthworm protein peptide provided by the present invention has effects of thrombosis inhibition, thrombolysis, anticoagulation and fibrinolysis promotion, and can effectively prevent and treat thrombotic diseases.

In order to achieve the above invention objective, the present invention provides application of an earthworm protein peptide in the preparation of a medicine for preventing and/or treating a thrombotic disease. The earthworm protein peptide is one or more therapeutic agents selected from the group consisting of a first earthworm protein peptide, a second earthworm protein peptide, a third earthworm protein peptide, and a fourth earthworm protein peptide; an amino acid sequence of the first earthworm protein peptide referenced herein as SEQ ID NO: 1; an amino acid sequence of the second earthworm protein peptide referenced herein as SEQ ID NO: 2; an amino acid sequence of the third earthworm protein peptide referenced herein as SEQ ID NO: 3; and an amino acid sequence of the fourth earthworm protein peptide referenced herein as SEQ ID NO: 4.

Preferably, the prevention and/or treatment of a thrombotic disease is implemented by thrombosis inhibition and/or thrombolysis and/or anticoagulation and/or fibrinolysis promotion.

Preferably, the medicine also includes pharmaceutically acceptable excipients.

Preferably, dosage forms of the medicine include powders, granules, pills, tablets, capsules, ointments or decoctions.

The beneficial effects of the present invention include application of an earthworm protein peptide in the preparation of a medicine for preventing and/or treating a thrombotic disease, which belongs to the technical field of prevention and treatment of cardiovascular and cerebrovascular diseases. The earthworm protein peptide is one or more members selected from the group consisting of Leu-Val-Thr-Leu-Gly-Asn-Glu (SEQ ID NO: 1), Leu-Leu-Ala-Pro-Pro (SEQ ID NO: 2), Leu-Leu-Pro-Ala-Pro (SEQ ID NO: 3) and Thr-Val-Ala-Pro-Phe (SEQ ID NO: 4). The earthworm protein peptide provided by the present invention has significant anticoagulant activity, and it can significantly inhibit the thrombin activity, thus achieving the anticoagulant effect. In vivo, the earthworm protein peptide provided by the present invention has a significant inhibitory effect on carrageenan-induced rat tail thrombosis. In in vitro and in vivo testing of rats with thrombus, the earthworm protein peptide provided by the present invention shows good anticoagulant effects. The earthworm protein peptide provided by the present invention has effects of thrombosis inhibition, thrombolysis, anticoagulation and fibrinolysis promotion, and it can effectively prevent and treat thrombotic diseases.

BRIEF DESCRIPTION OF THE DRAWINGS

FIGS. 6A-6D are diagrams showing results of mass spectrum identification of the several earthworm protein peptide components in Embodiment 1; wherein FIG. 6A shows the mass spectrum of earthworm protein peptide set forth in SEQ ID No. 1, FIG. 6B shows the mass spectrum of earthworm protein peptide set forth in SEQ ID No. 2, FIG. 6C shows the mass spectrum of earthworm protein peptide set forth in SEQ ID No. 3, and FIG. 6D shows the mass spectrum of earthworm protein peptide set forth in SEQ ID No. 4;

DESCRIPTION OF THE EMBODIMENTS

The present invention provides application of an earthworm protein peptide in the preparation of a medicine for preventing and/or treating a thrombotic disease. The earthworm protein peptide is one or more members selected from the group consisting of a first earthworm protein peptide, a second earthworm protein peptide, a third earthworm protein peptide, and a fourth earthworm protein peptide; an amino acid sequence of the first earthworm protein peptide corresponding to SEQ ID NO: 1, specifically: Leu-Val-Thr-Leu-Gly-Asn-Glu, wherein the molecular weight is 745.4 Da; an amino acid sequence of the second earthworm protein peptide corresponding to SEQ ID NO: 2, specifically: Leu-Leu-Ala-Pro-Pro, wherein the molecular weight is 510.3 Da; an amino acid sequence of the third earthworm protein peptide corresponding to SEQ ID NO: 3, specifically: Leu-Leu-Pro-Ala-Pro, wherein the molecular weight is 510.3 Da; an amino acid sequence of the fourth earthworm protein peptide corresponding to SEQ ID NO: 4, specifically: Thr-Val-Ala-Pro-Phe, wherein the molecular weight is 535.3 Da.

In the present invention, the prevention and/or treatment of a thrombotic disease is implemented preferably by thrombosis inhibition and/or thrombolysis and/or anticoagulation and/or fibrinolysis promotion.

In the present invention, the medicine preferably also includes pharmaceutically acceptable excipients.

In the present invention, dosage forms of the medicine preferably include powders, granules, pills, tablets, capsules, ointments or decoctions.

The technical effects provided by the present invention are described in detail below with reference to the embodiments, but the described embodiments should be construed as only illustrations and not as limiting the protection scope of the present invention.

Embodiment 1: Separation and Purification of an Earthworm Protein Peptide

The separation and purification of an earthworm protein peptide includes as one example the following steps:

1) 10 g of earthworm protein peptide (provided by Zhongshi Duqing (Shandong) Biotech Co., Ltd.) was provided, and 200 mL of 2% acetic acid aqueous solution was added and the solution was stirred and dissolved for 0.5 h. The earthworm protein peptide was centrifuged at a rate of 8000 r/min at 15° C. for 15 min, and filtered through a filter head with a pore diameter of 0.45 μm for later use.

2) Separation through a Sephadex G50 column was performed: an ultra-pure water balance column was used first for washing for 3-5 column volumes; and then samples were loaded, the column was washed with ultra-pure water at a rate of 2.5 mL/min for 2 h, components of the earthworm protein peptide having passed through a membrane were collected according to a chromatographic peak, and the components were concentrated and then freeze-dried into powder by using a vacuum dryer.

Figure 1:
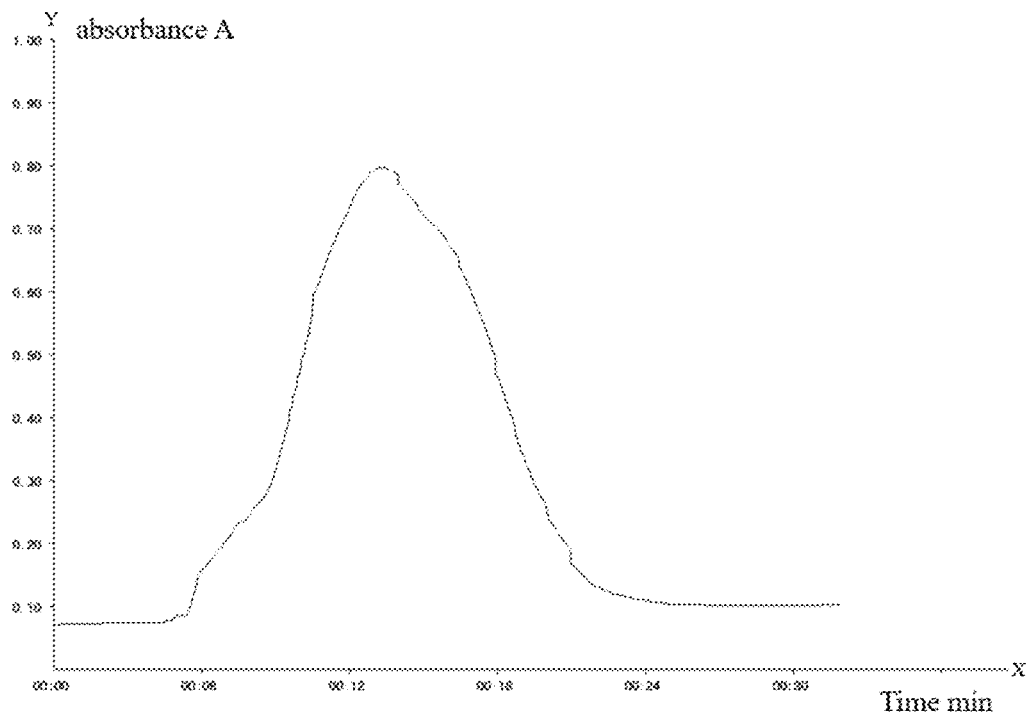
FIG. 1 is a separation chromatogram of an earthworm protein peptide in Embodiment 1 after separation through a Sephadex G50 chromatographic column.

The separation conditions were as follows: an eluent was ultrapure water; the elution time was 2 h; the elution rate was 2.5 mL/min; a chromatographic column was 600 mm by 25 mm; and the detection wavelength was 214 nm. See FIG. 1 for a separation chromatogram. It can be seen from FIG. 1 that the earthworm protein peptide was initially separated by a Sephadex G50 chromatographic column, and different components were collected according to absorbance.

Figure 2:
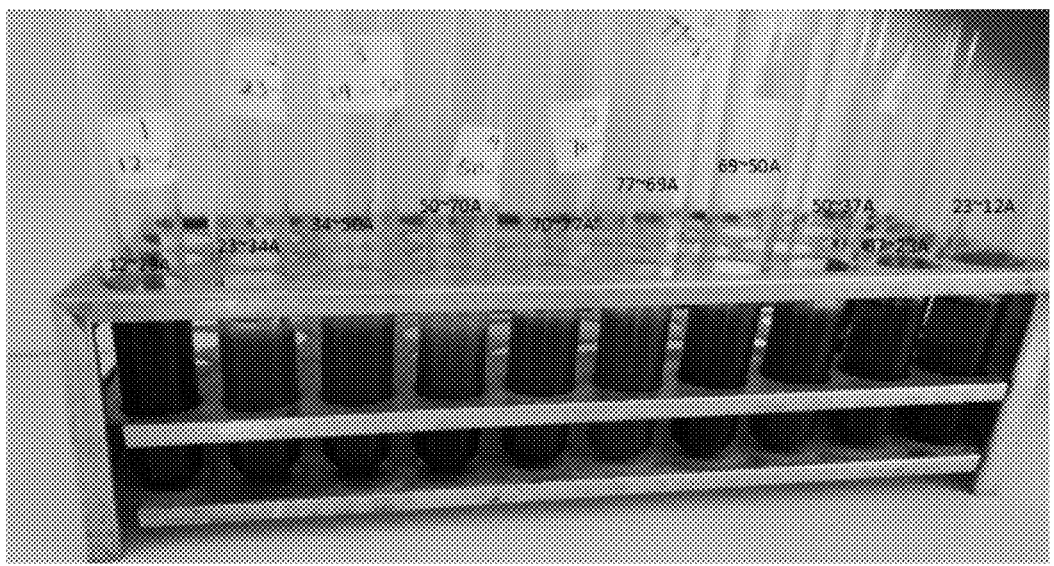
FIG. 2 is a diagram showing the anticoagulant effect of each of several fractions of the earthworm protein peptide in Embodiment 1 after separation through a Sephadex G50 chromatographic column.

3) The earthworm protein peptide was separated by the Sephadex G50 chromatographic column. FIG. 2 shows the real object diagrams of the components. The anticoagulant activity of different components collected was verified by a fibrin plate method and an anticoagulant test in vitro. The results showed that the anti-coagulation effect of the components with absorbance of 70 A-77 A was the best.

4) The earthworm protein peptide component having the best anticoagulant activity in step 3) was further separated and purified by a preparative liquid chromatograph. 10 mg of powder sample was weighed and placed into a 10 mL volumetric flask, 10 mL of pure water was added, and the powder sample was ultrasonically treated for dissolution. The sample solution passed through a membrane with a pore diameter of 0.45 μm before being measured by the liquid chromatograph.

Figure 3:
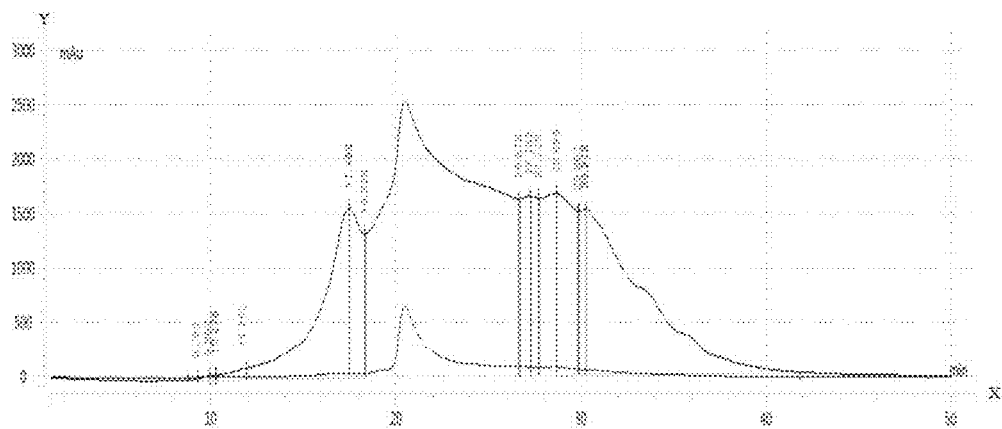
FIG. 3 is a chromatogram of earthworm protein peptide components in Embodiment 1 after separation and purification through a preparative liquid chromatograph.

Chromatographic conditions: the flow rate was 20 mL/min; the mobile phase proportion was 80% of buffer A to 20% of buffer B for a time of 0 min to 5 min; from 5 min to 35 min, the mobile phase ratio of 80% of buffer A to 20% of buffer B was changed to a mobile phase ratio of 20% of buffer A to 80% of buffer B; from 35 min to 40 min, the mobile phase ratio was 20% of buffer A to 80% of buffer B; the buffer A was 0.1% trifluoroacetic acid and water, and the buffer B was 0.1% trifluoroacetic acid and acetonitrile. FIG. 3 shows the preparative liquid chromatogram. It can be seen from FIG. 3 that the earthworm protein peptide was separated and purified by using a liquid phase preparation machine, components with peaks at different time periods were collected, and the anticoagulant effects of the components were determined by using the fibrin plate method.

Figure 4:
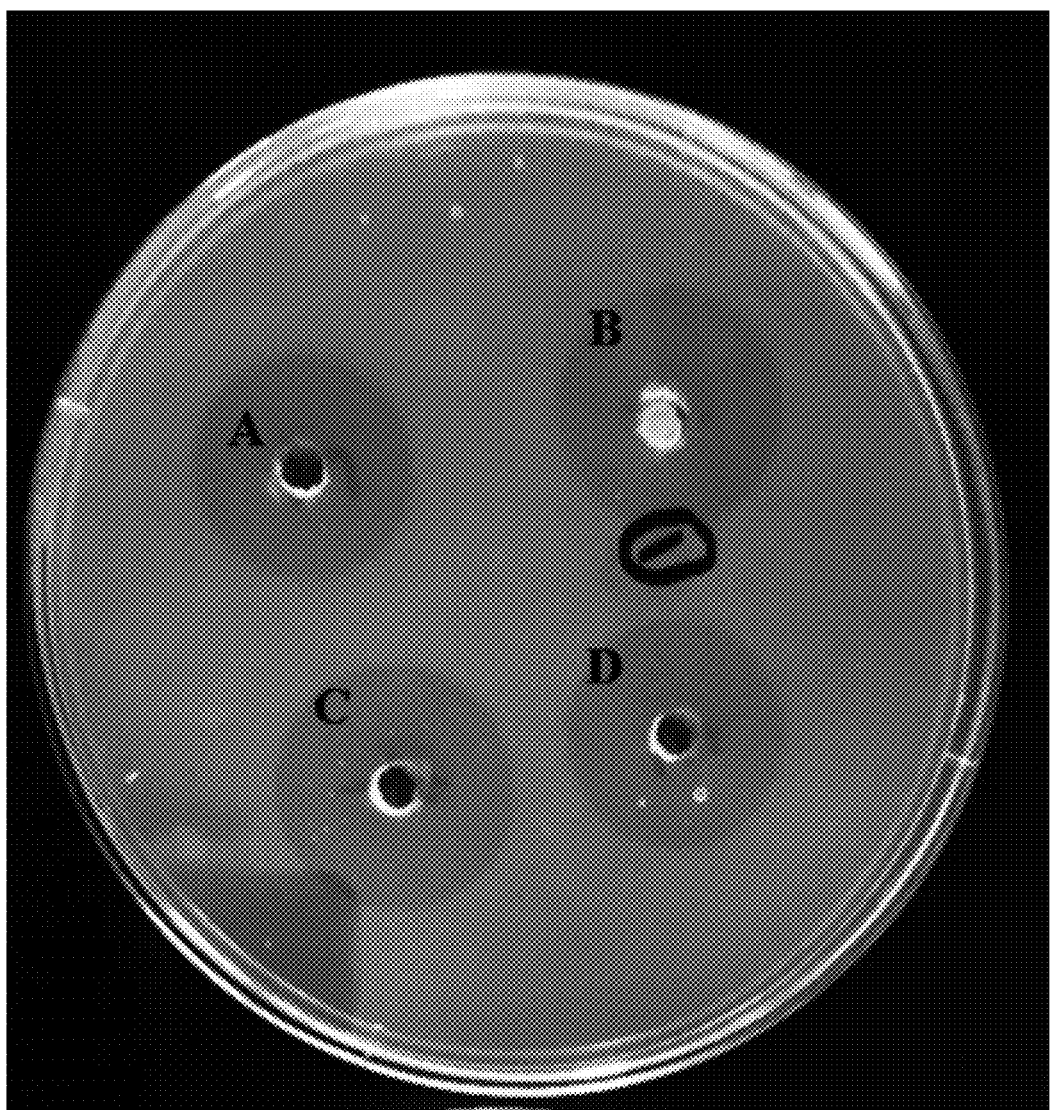
FIG. 4 is a diagram showing diameter measurement results of a precipitation coil in Embodiment 1.
Figure 5:
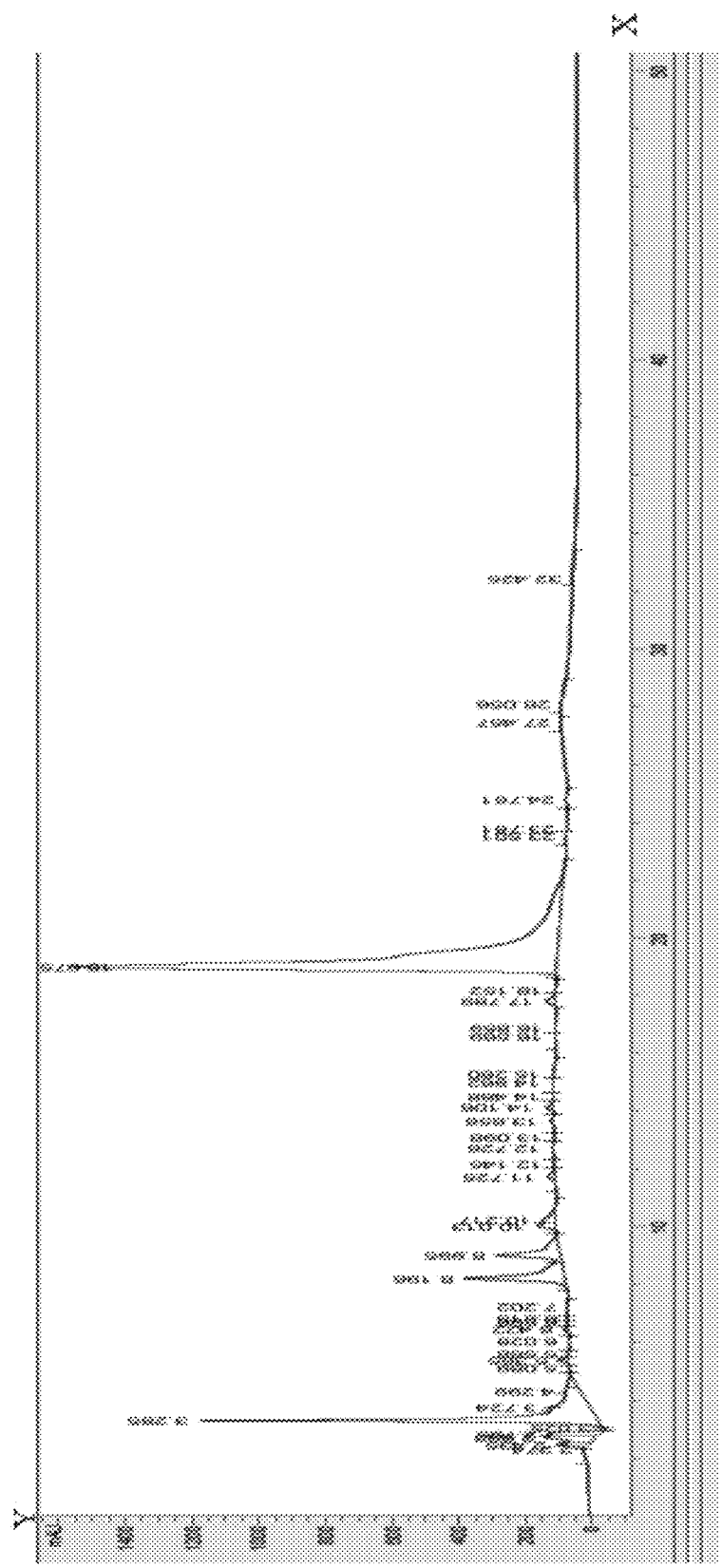
FIG. 5 is a chromatogram of the earthworm protein peptide in Embodiment 1 after separation and purification through an analytical liquid phase (Waters)(Bridge C18 column)
Figure 6A:
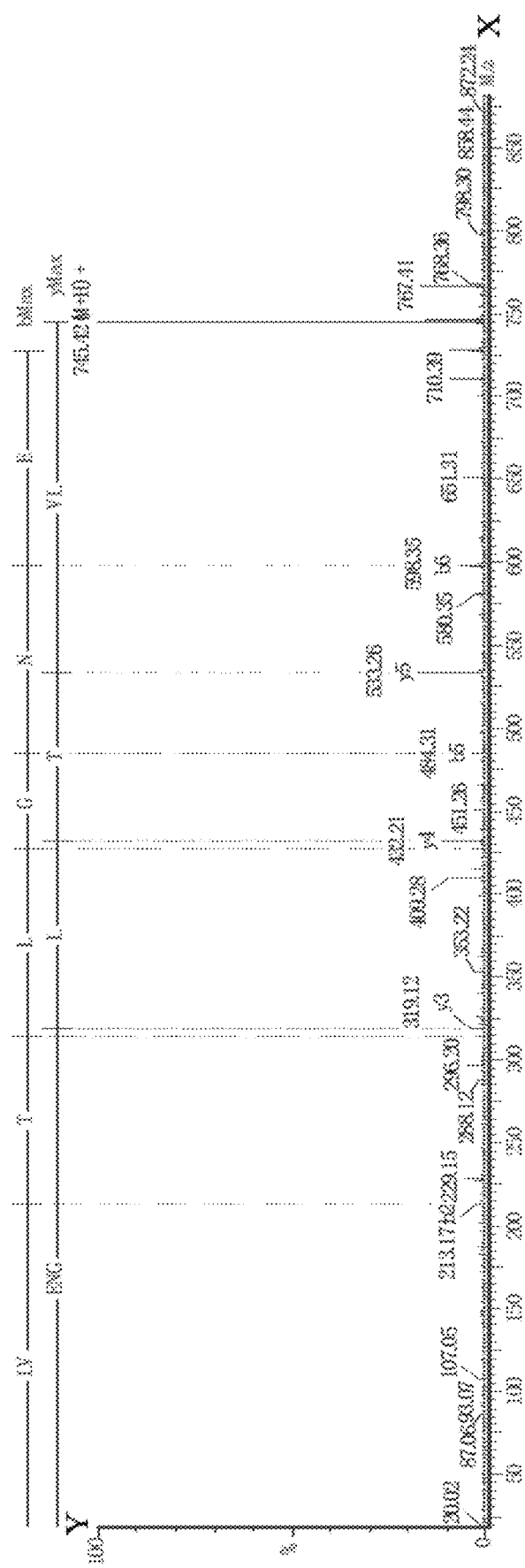
Figure 6B:
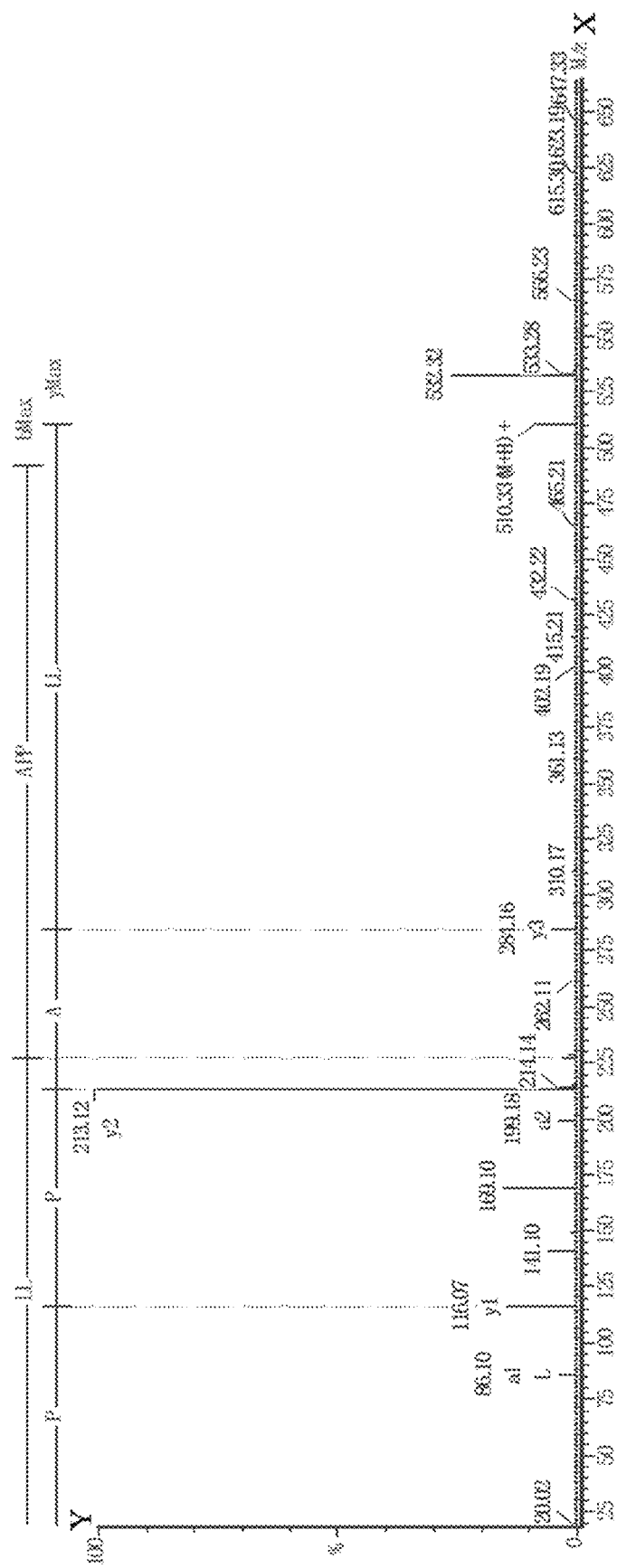
Figure 6C:
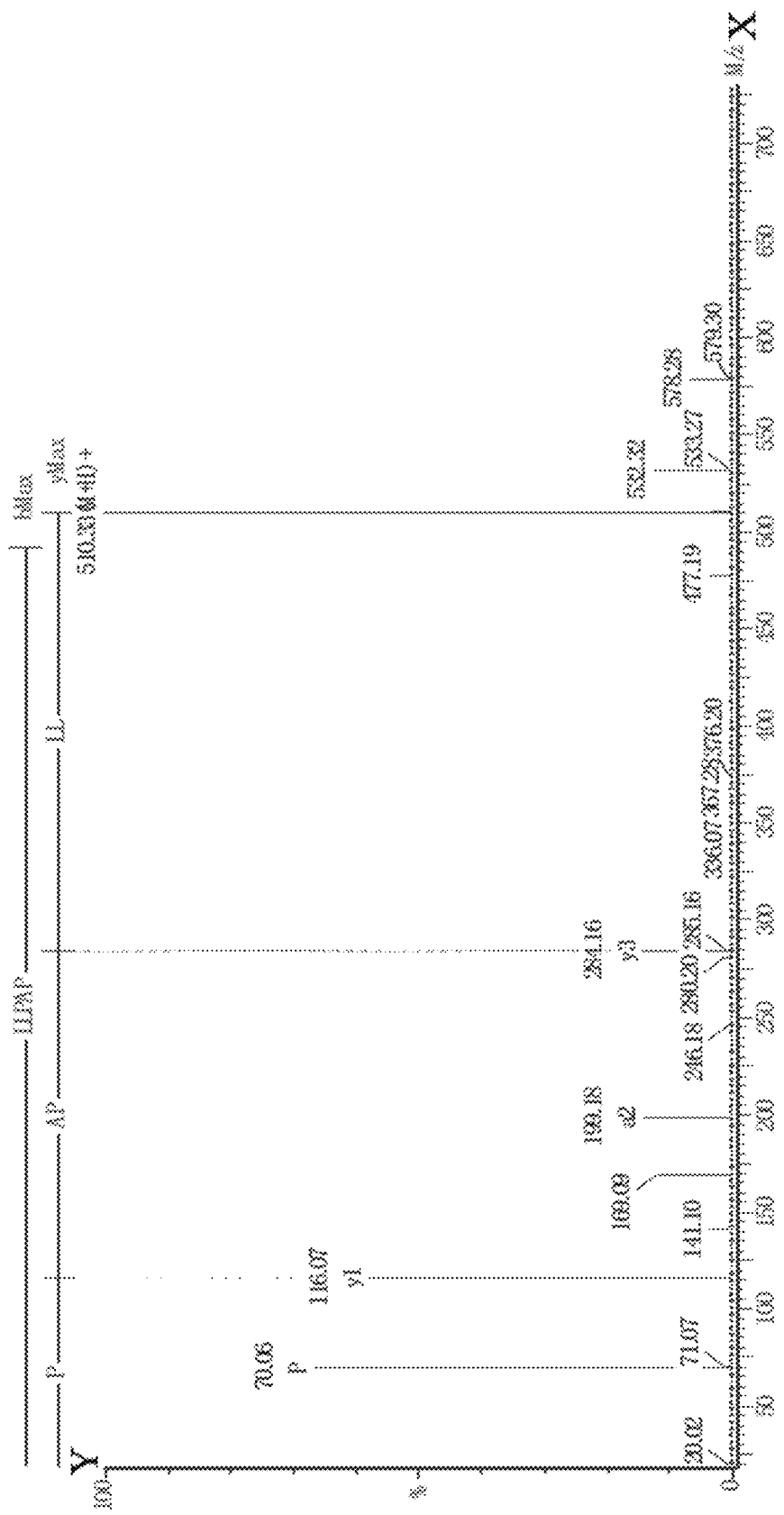
Figure 6D:
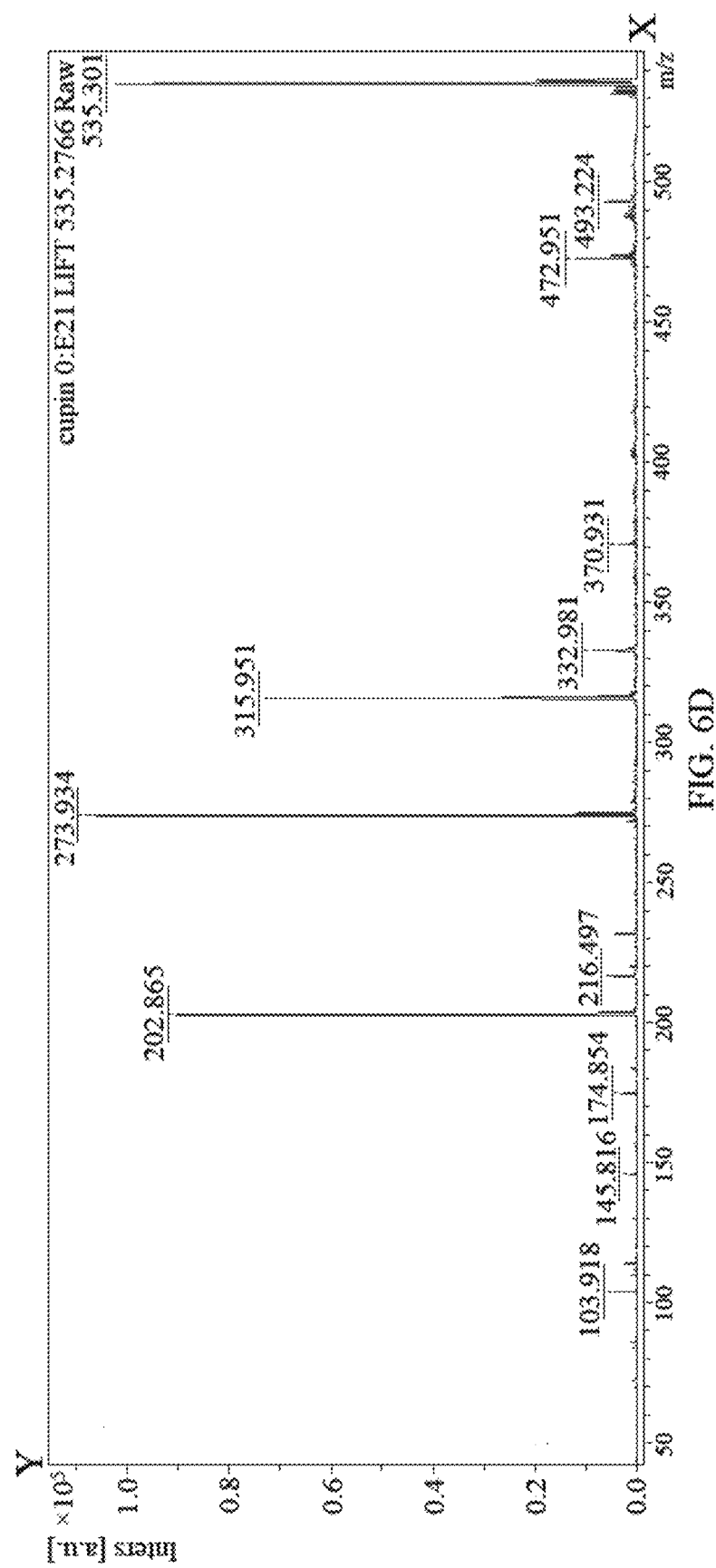

5) The anticoagulant activity of different components was verified by the fibrin plate method, and the anticoagulant effect was tested in vitro according to the different peaks collected. Specifically, fibrinogen was used as a substrate to perform immunodiffusion reaction on fibrinogen plates, the diameter of a precipitation coil was accurately measured, and the diameter of the precipitation coil was used to determine the thrombolytic activity of different components of earthworm protein peptides. Finally, the earthworm protein peptide was separated and purified through a liquid phase preparation machine (using a Waters)(Bridge C18 column (185 µm by 4.6 µm by 250 mm) with water-acetonitrile as a mobile phase at a flow rate of 0.8 ml/min. The earthworm protein peptide was separated and purified with a detection wavelength of 214 nm. Three components with good thrombolytic activity were detected and were labeled as component 3, component 4, and component 6 respectively. The next sequence determination was performed for these three components. FIG. 4 shows the diameter measurement result of the precipitation coil, where FIG. 4-A shows a thrombolytic coil of the component 3 (23-24 min); FIG. 4-B shows a thrombolytic coil of the component 4 (23-24 min); FIG. 4-C shows a lumbrokinase thrombolysis line; and FIG. 4-D shows a thrombolytic coil of the component 6 (29-32 min). As shown in FIG. 4, the components 3, 4 and 6 exhibit different diameters of thrombolytic coils, indicating that the components contain polypeptide components having good anticoagulant thrombolytic activity, which needs to be further analyzed and tested. FIG. 5 shows the purification results of a liquid phase preparation machine. It can be seen from FIG. 5 that the earthworm protein peptide has complex components when separated and purified, which needs to be processed in the next step.

6) The earthworm protein peptide components (the components labeled 3, 4, and 6) having the best anticoagulant activity in step 5) were further subjected to sequencing by a mass spectrometer.

Mass spectrometry conditions: chromatograph: WATERS ACQUITY UPLC; detector: WATERS ACQUITY PDA; detection wavelength: 520 nm; analytical column: BEH C18 2.1×100 mm 1.7 um; mobile phase: A: 1% formic acid, B: 100% acetonitrile; flow rate: 0.8 ml/min; detection wavelength: 214 nm; ion mode: ESI+; ion source temperature (Source Block Temp): 100° C.; desolation temperature: 400° C.; collision energy: collision energy (eV): 6/20 Volts; mass range: 20-1500 m/z; detector voltage: 1800 Volts. FIGS. 6A-6D show the mass spectrum identification results. It was found that the component 3, the component 4 and the component 6 contained four amino acid sequences with anticoagulant activity, respectively: Leu-Val-Thr-Leu-Gly-Asn-Glu (SEQ ID NO: 1), Leu-Leu-Ala-Pro-Pro (SEQ ID NO: 2), Leu-Leu-Pro-Ala-Pro (SEQ ID NO: 3) and Thr-Val-Ala-Pro-Phe (SEQ ID NO: 4).

Embodiment 2

1) Determination of Basic Physical and Chemical Properties of an Earthworm Protein Peptide Determination of protein content (GB5009.9-Kjeldahl azotometer), determination of moisture content (GB5009.3), determination of ash content (GB5009.4), and the measurement results are shown in Table 1.

TABLE 1

Results of determination of basic physical and chemical properties of an earthworm protein peptide

| Protein | Moisture | Ash |
| --- | --- | --- |
| 75.7% | 5.29% | 5.1% |

2) Analysis of Amino Acid Distribution in the Earthworm Protein Peptide

Figure 7:
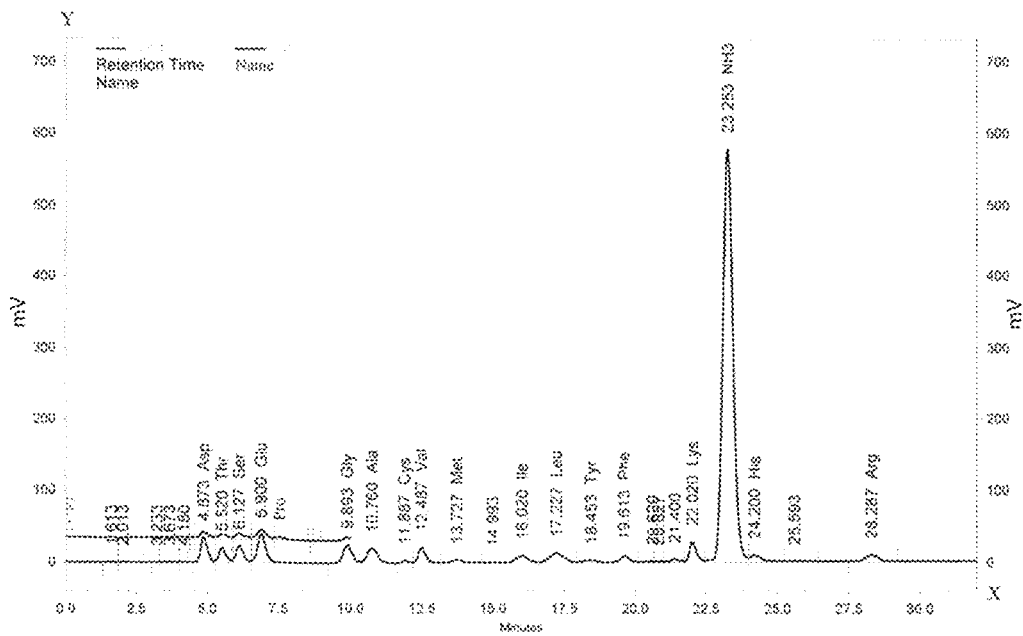
FIG. 7 is an analysis diagram of amino acid distribution in an earthworm protein peptide in Embodiment 2.

The amino acid composition of the earthworm protein peptide was analyzed by using a Hitachi L-8900 amino acid automatic analyzer. The analysis results are shown in FIG. 7. The distribution of the amino acid composition of the earthworm protein peptide can be seen in FIG. 7.

3) Determination of Amino Acid Distribution of the Earthworm Protein Peptide

Figure 8:
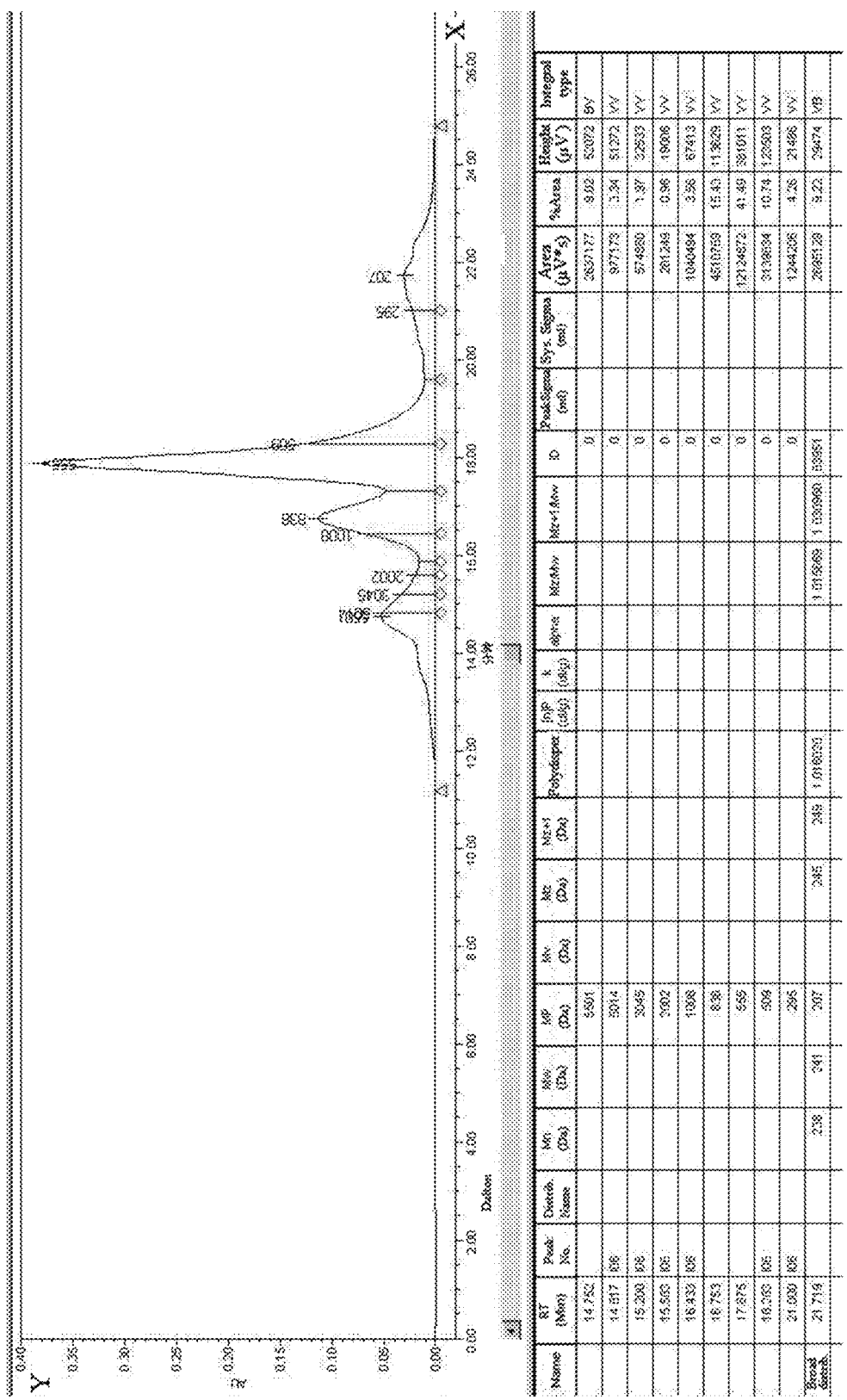
FIG. 8 is a diagram of a measurement result of molecular weight distribution of the earthworm protein peptide in Embodiment 2.

The molecular weight distribution of the earthworm protein peptide was determined using a Waters 2489 liquid chromatograph. The measurement results are shown in FIG. 8. As can be seen in FIG. 8, the molecular weight of the earthworm protein peptide was mainly concentrated below 1000 Da, indicating that it was small molecule polypeptide that mainly played a role in anticoagulant activity.

Embodiment 3: Inhibition of the Earthworm Protein Peptide on Carrageenan-Induced Rat Tail Thrombosis 1) Reagents and Instruments Carrageenan was supplied by Sagma Corporation; vernier caliper; stopwatch; scalpel; earthworm protein peptide, yellow powder, provided by provided by Zhongshi Duqing (Shandong) Biotech Co., Ltd.; aspirin, white flake, with the batch number of H51021360; Baiao lumbrokinase capsule, yellow capsule, with the batch number of H11021129; lidocaine hydrochloride injection, injection, with the batch number of H37022147.

Modeling Method

The carrageenan was weighed and prepared into a carrageenan solution (2%) with a concentration of 2 mg/mL using 0.9% NaCl; rats were weighed and injected with carrageenan subcutaneously at a dose of 80 mg/kg; intragastric administration treatment was performed on a prevention group 5 days in advance; after model making for 30 min, intragastric administration treatment was performed on the remaining four groups other than the prevention group according to relevant doses, and then the rats were placed in a constant temperature environment of (18±2)° C., and free diet and water drinking were provided.

A total of 42 SD rats were randomly selected for thrombus model making by using carrageenan. The physiological activities of the rats were observed. The normal saline was used as a blank control group, and an aspirin group was used as a positive control group. A polypeptide (the earthworm protein peptide containing four anticoagulant active polypeptides, namely Leu-Val-Thr-Leu-Gly-Asn-Glu, Leu-Leu-Ala-Pro-Pro, Leu-Leu-Pro-Ala-Pro and Thr-Val-Ala-Pro-Phe prepared in Embodiment 1) and relevant medicines were dissolved with normal saline, and the intragastric administration dose was operated according to Table 2 below. At 24, 36, 48, 60, 72, and 96 hours, the length of the thrombus black tail was measured with a vernier caliper, and the ratio of thrombus black tail was calculated. After injection of carrageenan in each experimental group and normal saline group, rats with different degrees of blood stasis and black tail appeared 3 to 14 hours after model making, and gradually expanded to the tail root. The measured data was processed by spss18.0 software. In order to compare the differences between different groups, one-way analysis of variance was used. The results showed that there were significant differences between different groups. If P was smaller than 0.05, it indicated there was significant difference. After 10 days of feeding, blood was taken from the inferior vena cava of the rats, and four items of blood coagulation and blood routine examination were performed. The test results are shown in Table 3 and Table 4 below and in FIGS. 9 to 23.

TABLE 2

Intragastric administration doses of each group

| Group | Type | Dose (mg/kg) |
|---|---|---|
| Normal saline group | Normal saline | — |
| Lumbrokinase group | Lumbrokinase | 61.73 |
| Low-dose group | Earthworm protein peptide | 123.46 |
| Medium-dose group | Earthworm protein peptide | 246.92 |
| High-dose group | Earthworm protein peptide | 493.84 |
| Aspirin group | Aspirin | 7.72 |
| Prevention group | Earthworm protein peptide | 493.84 |

TABLE 3

Black tail rates of rats in different groups

| Group | Dose (mg/kg) | Black tail rates of rats (%) | | | | | |
|---|---|---|---|---|---|---|---|
| | | 24 h | 36 h | 48 h | 56 h | 72 h | 96 h |
| Normal saline group | — | 16.7% | 66.70% | 83.30% | 100% | 100% | 100% |
| Lumbrokinase group | 61.73 | 0 | 16.7% | 33.40% | 33.40% | 67% | 83.30% |
| Low-dose group | 123.46 | 0 | 33.40% | 33.40% | 33.40% | 67% | 83.30% |
| Medium-dose group | 246.92 | 0 | 16.7% | 16.7% | 16.7% | 16.7% | 83.30% |
| High-dose group | 493.84 | 0 | 33.40% | 33.40% | 33.40% | 83.30% | 100% |
| Aspirin group | 7.72 | 0 | 16.7% | 16.7% | 16.7% | 50% | 67% |
| Prevention group | 493.94 | 0 | 0.00% | 0.00% | 16.7% | 50% | 67% |

Table 3 shows the black tail rates of rats in different groups. As shown in Table 3, the black tail rate of the normal saline group reached 83.3% after 48 hours; the black tail rate of the lumbrokinase group, the low-dose group and the high-dose group respectively was 33.4%; the black tail rate of the medium-dose group and the aspirin group was 16.7%; and black-tailed rats did not appear (0.00%) in the prevention group.

TABLE 4

Data of four items of blood coagulation and blood routine examination of rats in different groups

| Group | Dose (mg/kg) | Activated Partial Thromboplastin Time (APTT) (s) | Fibrinogen concentration FIB(g/L) |
|---|---|---|---|
| Lumbrokinase group | 61.73 | 20.3 | 2.41 |
| Low-dose group | 123.46 | 24.9 | 2.199 |
| Medium-dose group | 246.92 | 26.6 | 2.65 |
| High-dose group | 493.84 | 25.2 | 2.23 |
| Normal saline group | — | 16.6 | 3.45 |
| Prevention group | 493.84 | 24.5 | 2.1 |

Table 4 shows data of four items of blood coagulation and blood routine examination of blood of rats in different groups. It can be seen from Table 4 that compared with the normal control group, the normal saline group significantly shortened the activated partial prothrombin time (APPT) of blood of rats (P<0.01), and significantly increased the fibrinogen (Fib) content (P<0.01), and those differences were statistically significant. Compared with the normal saline group, the high-dose group and the low-dose group prolonged APPT and reduced the Fib content, where the APPT of the high-dose group was significantly prolonged (P<0.05), the Fib content was significantly reduced (P<0.05), and those differences were also statistically significant. The results show that the earthworm protein peptide enhances the fibrinolytic function of the body and has the effect of preventing and inhibiting thrombosis.

Figure 9:
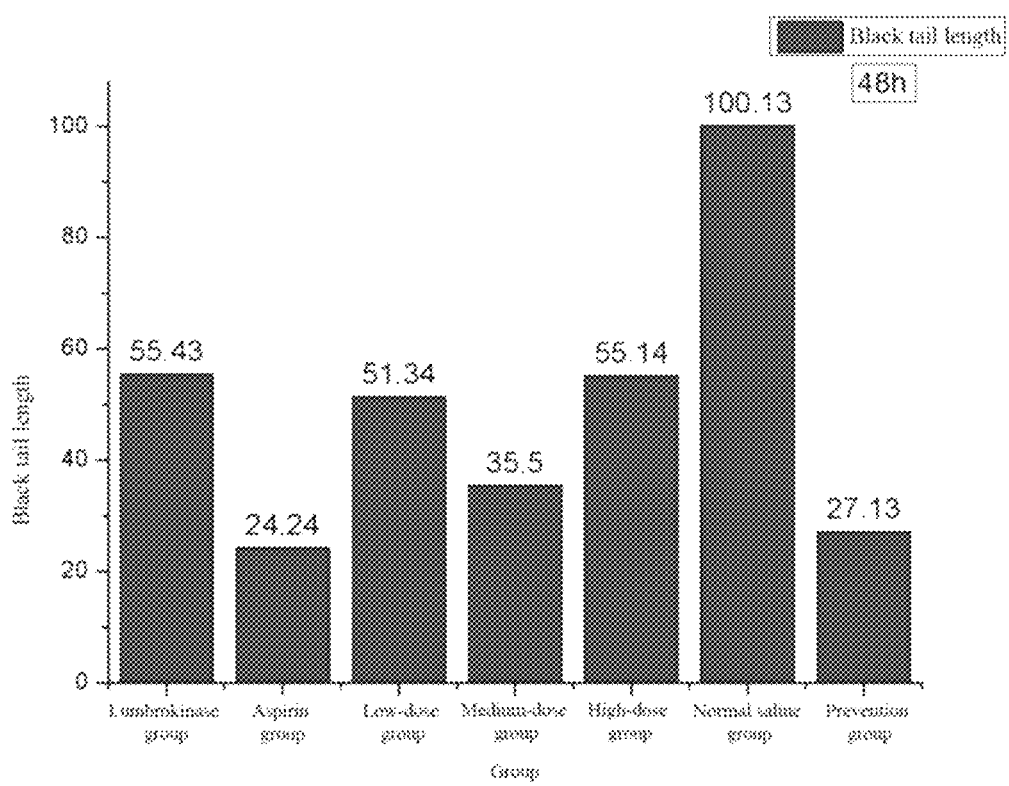
FIG. 9 is a histogram of lengths of tail thrombogenesis of each group of rats in Embodiment 3 after 48 hours.

FIG. 9 is a histogram of lengths of tail thrombogenesis of each group of rats after 48 hours. As shown in FIG. 9, the normal saline group had the highest black tail ratio and the greatest black tail length (100.13 mm). Compared with the normal saline group, the black tail inhibition ratios were as follows: the lumbrokinase group (44.6%), the aspirin group (75.8%), the low-dose group (48.78%), the medium-dose group (64.5%), the high-dose group (44.9%), and the prevention group (72.9%). Compared with normal saline, the earthworm protein peptide has significant therapeutic effects as well as the prevention of thrombosis. Other groups were significantly different from the normal saline group (P<0.01). The prevention group (27.13 mm) had the best treatment effect, and had no significant difference (P>0.05) with the aspirin group (24.24 mm); the medium-dose group (35.5 mm) took the second place, and the therapeutic effect of the low-dose group (51.34 mm) and the high-dose group (55.14 mm) was equivalent to that of the lumbrokinase group (55.43 mm), and there was no significant difference (P<0.01).

Figure 10:
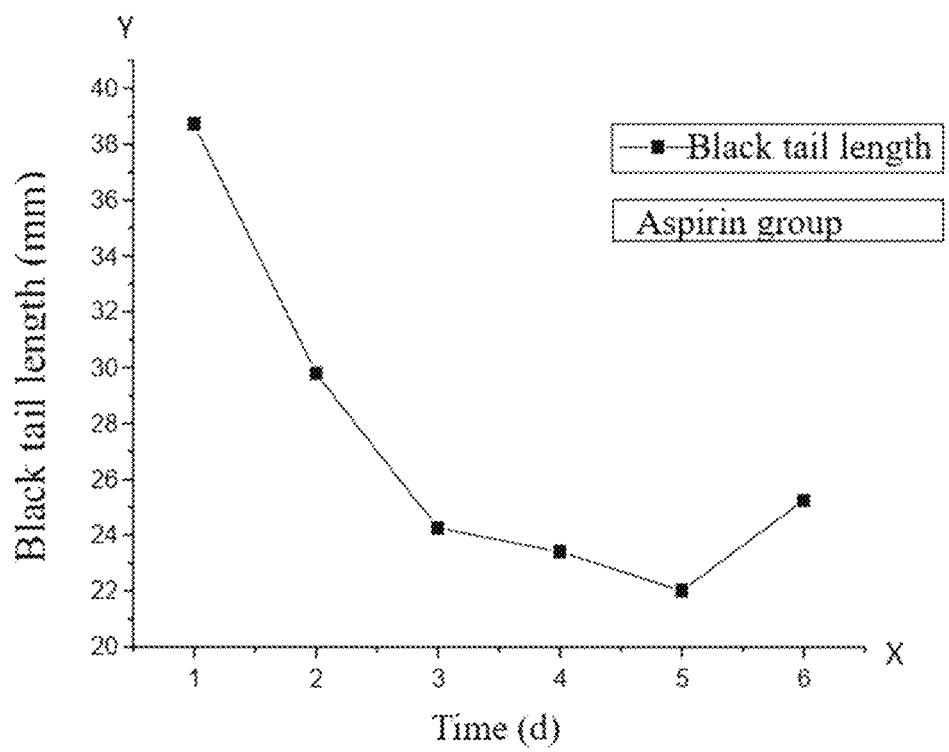
FIG. 10 is a broken line graph of thrombus black tail lengths of rats of an aspirin group corresponding to different times in Embodiment 3.
Figure 11:
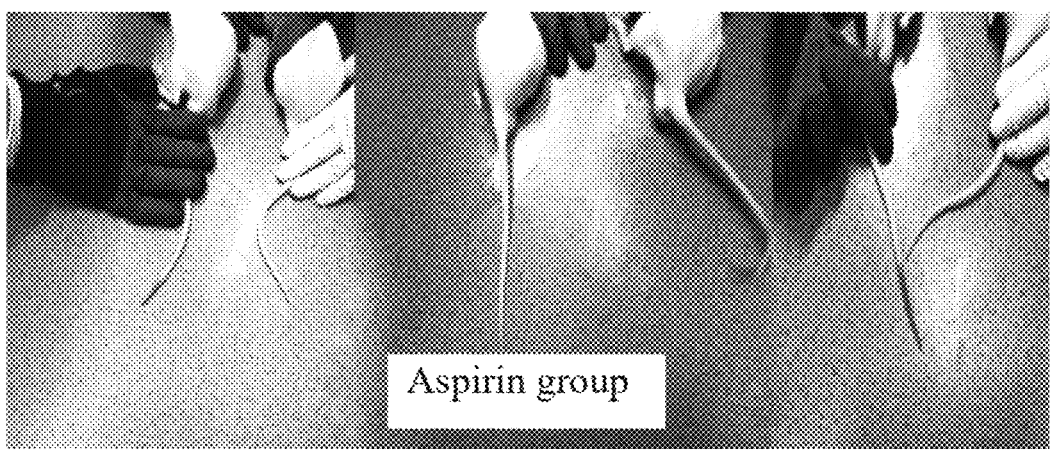
FIG. 11 shows a black tail state of rats of the aspirin group in Embodiment 3 after 72 hours.

FIG. 10 is a broken line graph of thrombus black tail lengths of rats of an aspirin group corresponding to different times; and FIG. 11 shows a black tail state of rats of the aspirin group after 72 hours. It can be observed from FIG. 10 that the SD rats had obvious inhibition effects on thrombus in the first 5 days, and the black tail lengths of the rats increased significantly on the 6th day. The subsequent analysis showed that this had a close relationship with the self-anticoagulation mechanism; and, as can be observed in FIG. 11, only three rats had obvious black tail signs after 72 hours.

Figure 12:
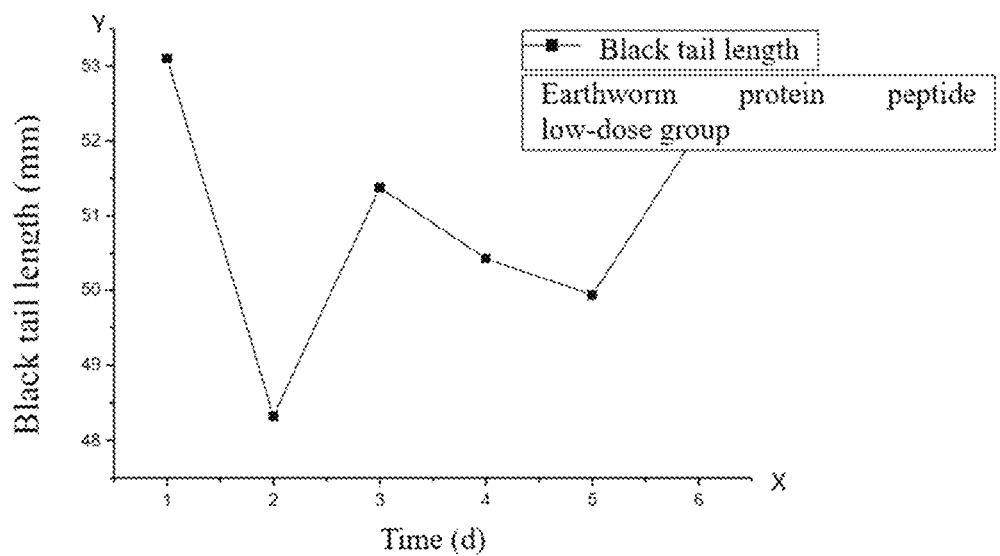
FIG. 12 is a broken line graph of thrombus black tail lengths of rats of an earthworm protein peptide low-dose group corresponding to different times in Embodiment 3.
Figure 13:
FIG. 13 shows a black tail state of rats of the earthworm protein peptide low-dose group in Embodiment 3 after 72 hours.

FIG. 12 is a broken line graph of thrombus black tail lengths of rats of an earthworm protein peptide low-dose group corresponding to different times; and FIG. 13 shows a black tail state of rats of the earthworm protein peptide low-dose group after 72 hours. It can be observed from FIG. 12 that black tail lengths of rats of the earthworm protein peptide low-dose group fluctuated obviously, and the overall black tail length was obviously reduced. It can be observed from FIG. 13 that, after 72 hours, four rats in the earthworm protein peptide low-dose group had an obvious black tail sign, the tails of two other rats had obvious signs of thrombus, and the earthworm protein peptide low-dose group had obvious antithrombotic therapy effects compared with the normal saline group.

Figure 14:
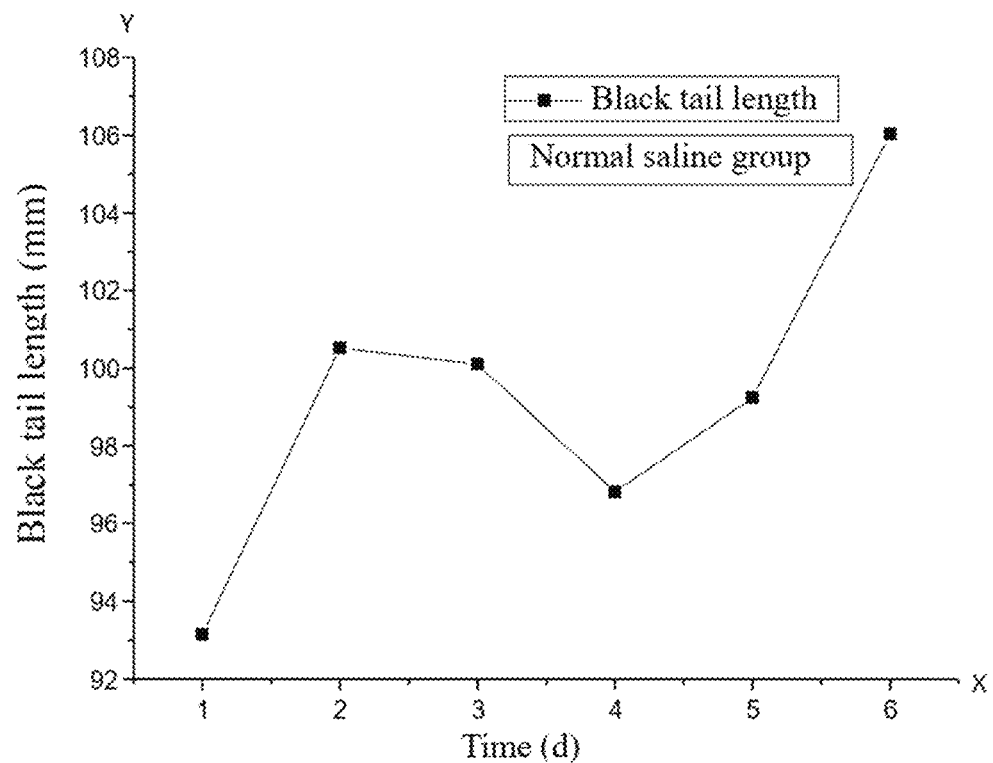
FIG. 14 is a broken line graph of thrombus black tail lengths of rats of a normal saline group corresponding to different times in Embodiment 3.
Figure 15:
FIG. 15 shows a black tail state of rats of the normal saline group in Embodiment 3 after 72 hours.

FIG. 14 is a broken line graph of thrombus black tail lengths of rats of a normal saline group corresponding to different times; and FIG. 15 shows a black tail state of rats of the normal saline group after 72 hours. It can be observed from FIG. 14 that black tail lengths of rats of the normal saline group changed obviously, which was related to its own anti-coagulation mechanism. The overall black tail length increased continuously, the black tail length reached the maximum on the sixth day after molding, and a broken tail sign appeared on the tenth day [Note: the results for the tenth day are not shown in FIG. 14.] after model making. It can be observed from FIG. 15 that after 72 hours, five rats of the normal saline group had a black tail condition, one of the rats had an obvious thrombus sign and black tail appeared on the second day. SPSS software showed that the normal saline group and the other six groups had significant differences ($P<0.01$).

Figure 16:
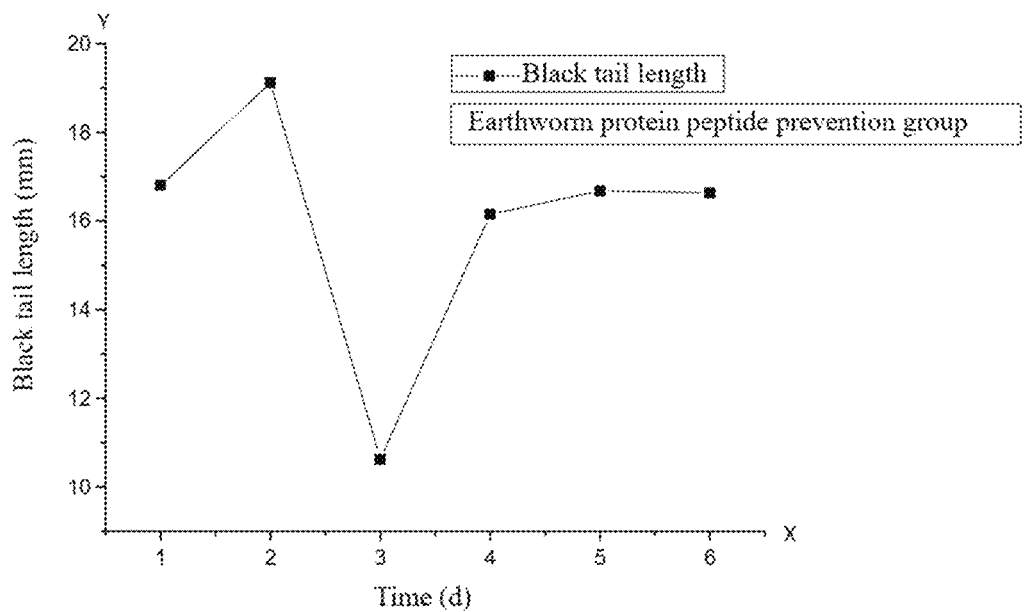
FIG. 16 is a broken line graph of thrombus black tail lengths of rats of an earthworm protein peptide prevention group corresponding to different times in Embodiment 3.
Figure 17:
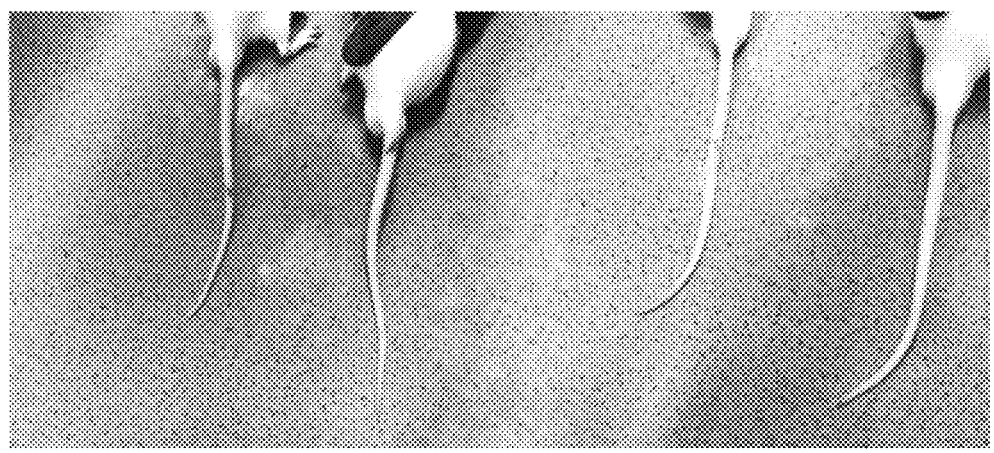
FIG. 17 shows a black tail state of rats of the earthworm protein peptide prevention group in Embodiment 3 after 72 hours.

FIG. 16 is a broken line graph of thrombus black tail lengths of rats of an earthworm protein peptide prevention group corresponding to different times; and FIG. 17 shows a black tail state of rats of the earthworm protein peptide prevention group after 72 hours. It can be observed from FIG. 16 that the black tail length of the earthworm protein peptide prevention group was the shortest, and the earthworm protein peptide had a remarkable positive effect on thrombus treatment and prevention. It was subsequently observed that the black tail length increased slightly, there was no casualty, and the overall treatment effect was the best. It can be observed from FIG. 17 that, after 72 hours, only one rat in the earthworm protein peptide prevention group had a black tail sign, the remaining three had obvious thrombus signs, and two rats were killed or injured within 48 hours after model making. No inflammatory death was found by anatomical observation. At the same time, it was observed that the reason of injury and death caused by model making was excluded for other groups of rats.

Figure 18:
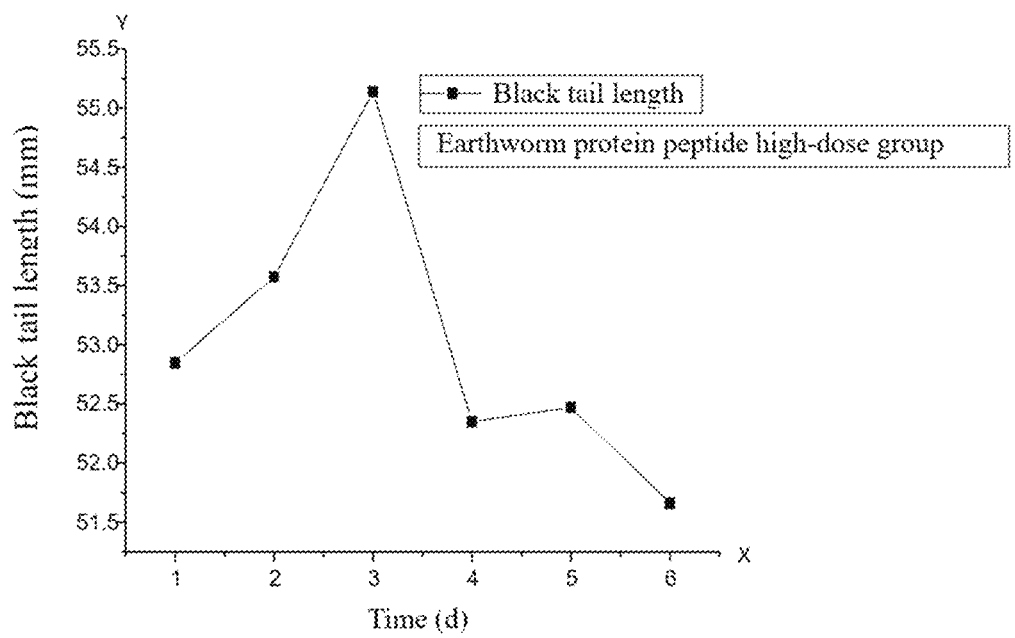
FIG. 18 is a broken line graph of thrombus black tail lengths of rats of an earthworm protein peptide high-dose group corresponding to different times in Embodiment 3.
Figure 19:
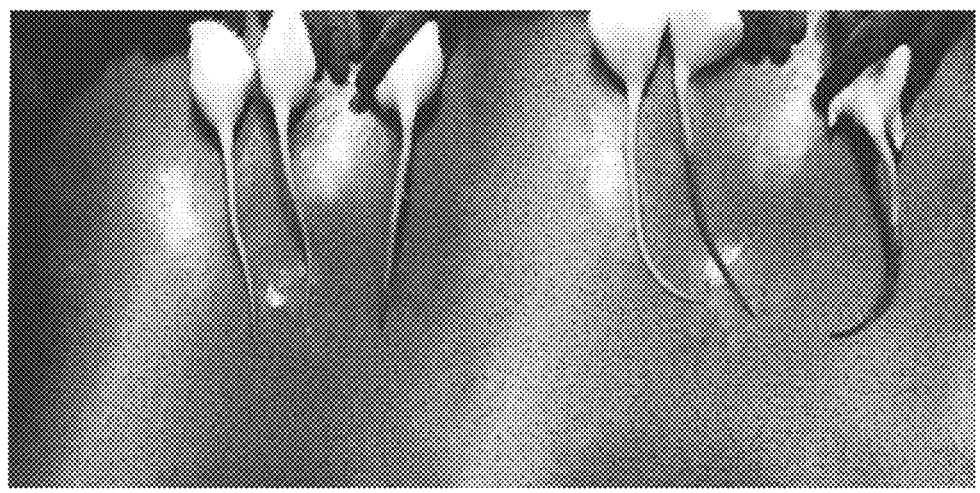
FIG. 19 shows a black tail state of rats of the earthworm protein peptide high-dose group in Embodiment 3 after 72 hours.

FIG. 18 is a broken line graph of thrombus black tail lengths of rats of an earthworm protein peptide high-dose group corresponding to different times; and FIG. 19 shows a black tail state of rats of the earthworm protein peptide high-dose group after 72 hours. It can be observed from FIG. 18 that the black tail lengths of rats of the earthworm protein peptide high-dose group after 72 hours reached the maximum value, the black tail length was controlled on the fourth day, and the black tail length became obviously small, which was a remarkable difference from the normal saline group ($P<0.01$). It can be observed from FIG. 19 that after 72 hours, three rats in the earthworm protein peptide high-dose group had an obvious black tail condition, and two rats had a slight black tail.

Figure 20:
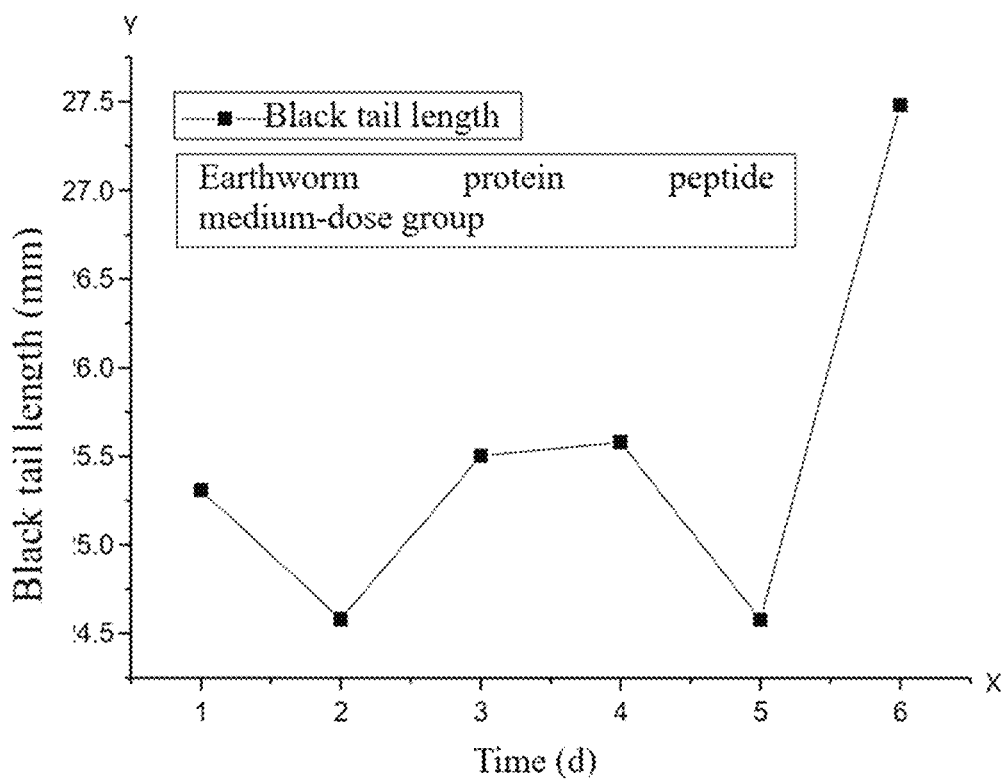
FIG. 20 is a broken line graph of thrombus black tail lengths of rats of an earthworm protein peptide medium-dose group corresponding to different times in Embodiment 3.
Figure 21:
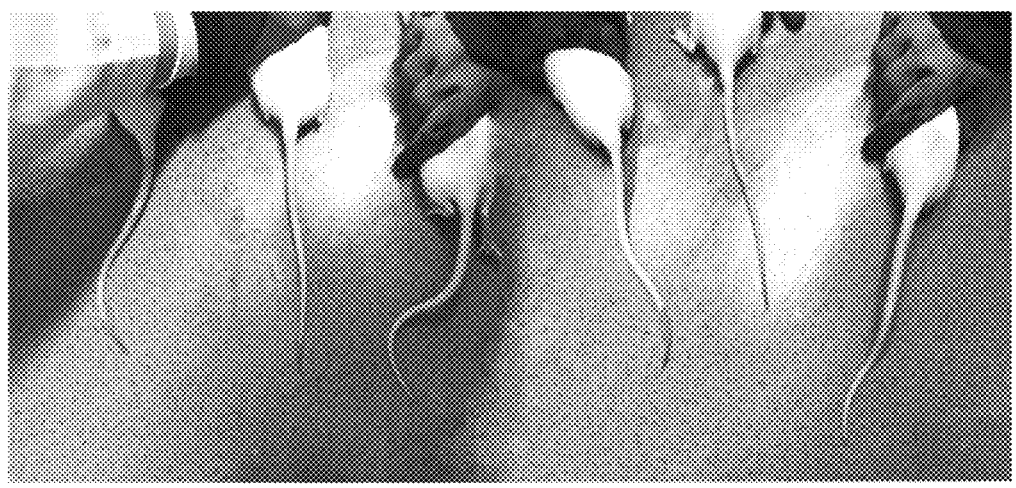
FIG. 21 shows a black tail state of rats of the earthworm protein peptide medium-dose group in Embodiment 3 after 72 hours.

FIG. 20 is a broken line graph of thrombus black tail lengths of rats of an earthworm protein peptide medium-dose group corresponding to different times; and FIG. 21 shows a black tail state of rats of the earthworm protein peptide medium-dose group after 72 h. It can be observed from FIG. 20 that the black tail lengths of rats in the earthworm protein peptide medium-dose group fluctuated obviously, the black tail length was increased obviously on the sixth day after model making, but the overall black tail length was short. Thus, the medium-dose earthworm protein peptide had an obvious antithrombotic therapy effect compared with the normal saline group. It can be observed from FIG. 21 that, after 72 hours, four rats in the earthworm protein peptide medium-dose group had obvious black tail signs, and two other rats had obvious thrombus signs. The therapeutic effect of this group was second only to the prevention group, which is obviously convincing for dosing a patient in this way in the future.

Figure 22:
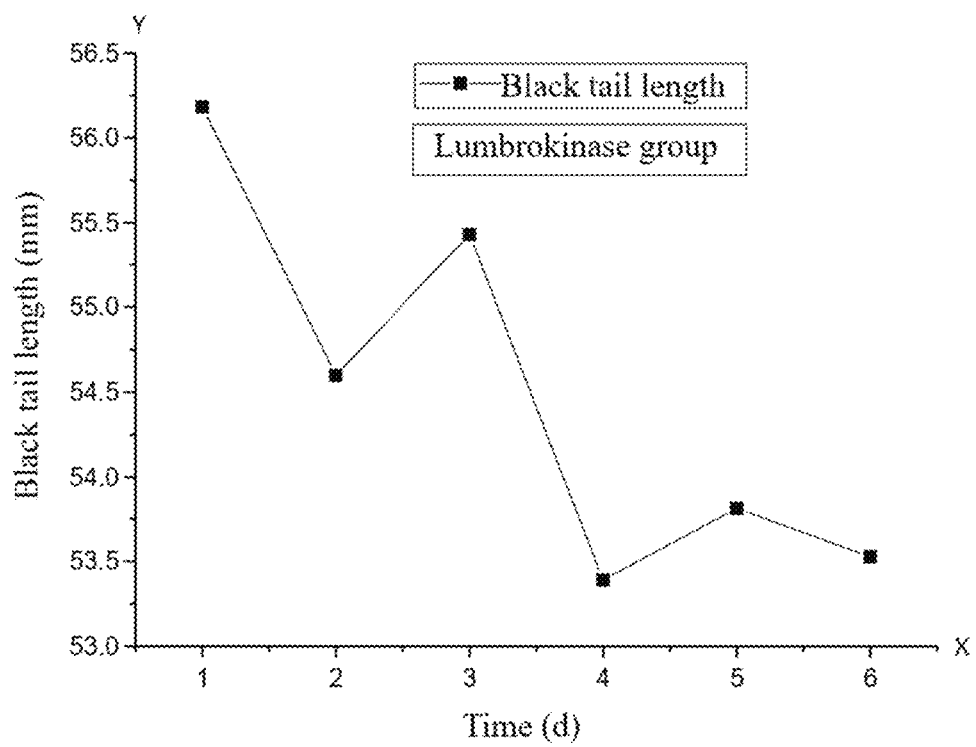
FIG. 22 is a broken line graph of thrombus black tail lengths of rats of a lumbrokinase group corresponding to different times in Embodiment 3.
Figure 23:
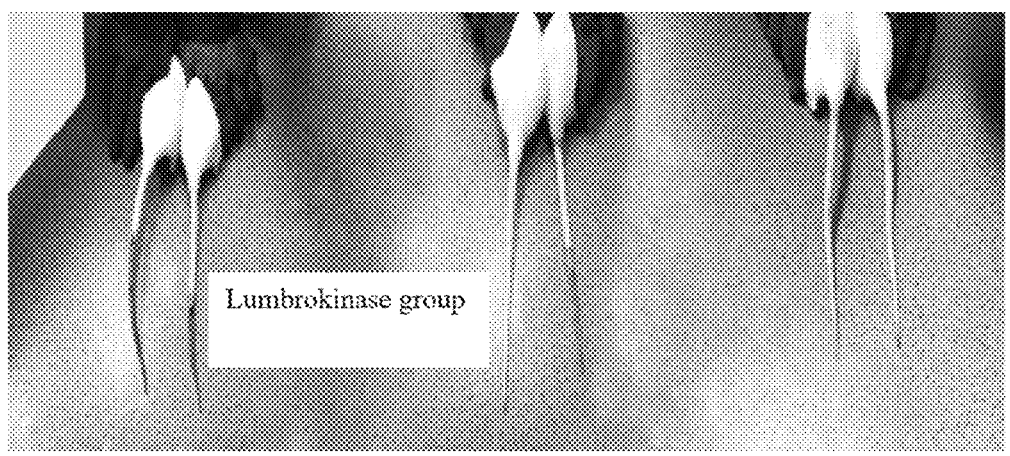
FIG. 23 shows a black tail state of rats of the lumbrokinase group in Embodiment 3 after 72 hours.

FIG. 22 is a broken line graph of thrombus black tail lengths of rats of a lumbrokinase group corresponding to different times; and FIG. 23 shows a black tail state of rats of the lumbrokinase group after 72 hours. It can be observed from FIG. 22 that the thrombus treatment effect of the lumbrokinase group was similar to that of the earthworm protein peptide low-dose group and that of the earthworm protein peptide high-dose group. The black tail length at the time of 72 hours after model making reached the maximum value, and the black tail lengths of treated rats were controlled. It can be observed from FIG. 23 that, after 72 hours, three rats in the lumbrokinase group had an obvious black tail sign, and two other rats had a slight black tail sign.

The above description was only of certain preferred embodiments of the present invention, and it should be understood that those skilled in the art can also make several improvements and modifications without departing from the principles of the present invention. These improvements and modifications should also be considered as falling within the scope of protection of the present invention.

What is claimed is:

1. A method for treating a thrombotic disease, comprising the step of administering a medicine containing an earthworm protein peptide to a patient in need, wherein:
the earthworm protein peptide contains at least one member selected from the group consisting of a first earthworm protein peptide, a second earthworm protein peptide, a third earthworm protein peptide, and a fourth earthworm protein peptide; wherein,
the amino acid sequence of the first earthworm protein peptide is set forth in SEQ ID NO: 1;
the amino acid sequence of the second earthworm protein peptide is set forth in SEQ ID NO: 2;
the amino acid sequence of the third earthworm protein peptide is set forth in SEQ ID NO: 3; and
the amino acid sequence of the fourth earthworm protein peptide is set forth in SEQ ID NO: 4.

2. The method according to claim 1, wherein treating the thrombotic disease is implemented by thrombosis inhibition and/or thrombolysis and/or anticoagulation and/or fibrinolysis promotion.

3. The method according to claim 1, wherein the medicine further comprises pharmaceutically acceptable excipients.

4. The method according to claim 1, wherein the medicine is administered in a dosage form selected from the group consisting of powders, granules, pills, tablets, capsules, ointments or decoctions.

5. The method according to claim 1, wherein the earthworm protein peptide contains the amino acid sequence of the first earthworm protein peptide set forth in SEQ ID NO: 1.

6. The method according to claim 1, wherein the earthworm protein peptide contains the amino acid sequence of the second earthworm protein peptide set forth in SEQ ID NO: 2.

7. The method according to claim 1, wherein the earthworm protein peptide contains the amino acid sequence of the third earthworm protein peptide set forth in SEQ ID NO: 3.

8. The method according to claim 1, wherein the earthworm protein peptide contains the amino acid sequence of the fourth earthworm protein peptide set forth in SEQ ID NO: 4.

9. A method for treating a thrombotic disease, comprising the step of administering a medicine consisting essentially of an earthworm protein peptide to a patient in need, wherein the earthworm protein peptide consists essentially of at least one member selected from the group consisting of a first earthworm protein peptide, a second earthworm protein peptide, a third earthworm protein peptide, and a fourth earthworm protein peptide; wherein, the amino acid sequence of the first earthworm protein peptide is set forth in SEQ ID NO: 1;

the amino acid sequence of the second earthworm protein peptide is set forth in SEQ ID NO: 2;

the amino acid sequence of the third earthworm protein peptide is set forth in SEQ ID NO: 3; and the amino acid sequence of the fourth earthworm protein peptide is set forth in SEQ ID NO: 4.

* * * * *